(12) United States Patent
Atkinson et al.

(10) Patent No.: US 7,732,617 B2
(45) Date of Patent: Jun. 8, 2010

(54) TOCOPHEROL DERIVATIVES AND USES THEREOF

(75) Inventors: Jeffrey Atkinson, St. Catharines (CA); Robert S. Parker, Dryden, NY (US); Stephan Ohnmacht, Edinburgh (GB); Phillip John Nava, Welland (CA); Ryan West, Welland (CA)

(73) Assignees: Brock University, St. Catharines, Ontario (CA); Cornell University, Ithaca, NY (US)

( * ) Notice: Subject to any disclaimer, the term of this patent is extended or adjusted under 35 U.S.C. 154(b) by 0 days.

(21) Appl. No.: 11/802,787

(22) Filed: May 25, 2007

(65) Prior Publication Data

US 2008/0293792 A1 Nov. 27, 2008

(51) Int. Cl.
| | |
|---|---|
| C07D 233/64 | (2006.01) |
| C07D 235/04 | (2006.01) |
| A61K 31/4178 | (2006.01) |
| A61K 31/4184 | (2006.01) |
| A61P 29/00 | (2006.01) |
| A61P 3/10 | (2006.01) |
| A61P 35/00 | (2006.01) |
| A61P 9/10 | (2006.01) |

(52) U.S. Cl. .................. 548/110; 514/397; 514/394; 548/305.1; 548/311.4

(58) Field of Classification Search .................. 548/110, 548/311.4, 310.1, 305.1
See application file for complete search history.

(56) References Cited

FOREIGN PATENT DOCUMENTS

| EP | 0 677 520 A1 | 10/1995 |
|---|---|---|
| WO | WO 00/01685 | 1/2000 |
| WO | WO 03/043570 | 5/2003 |
| WO | WO 2005/035491 | 4/2005 |
| WO | WO 2005/039443 | 5/2005 |

OTHER PUBLICATIONS

Slide entitled "Inhibition of P450-mediated tocopherol metabolism" presented at a seminar at the University of Pittsburgh, Department of Environmental and Occupational Health, Pittsburgh, PA, US (May 25, 2006): "The Bioorganic Chemistry of Vitamin E: New Tools and Approaches (or Rancid Fat, Hand Cream, and Snake Oil)". (print of slide enclosed).

*Primary Examiner*—James O Wilson
*Assistant Examiner*—Cecilia M Jaisle
(74) *Attorney, Agent, or Firm*—Dennison, Schultz & MacDonald

(57) ABSTRACT

Tocopherol derivatives having the general formula:

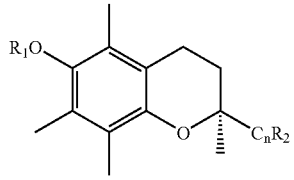

wherein n is an integer of 6 to 13, $R_1$ is hydrogen, a silyl ether or acetate, $R_2$ is an optionally substituted nitrogen-containing heterocycle or a polycyclic nitrogen-containing heterocycle; and pharmaceutically acceptable salts thereof are provided. A method for synthesizing the compounds is also provided. The tocopherol derivatives are capable of inhibiting the primary enzyme responsible for the metabolism of the tocopherols and tocotrienols compounds of vitamin E, namely tocopherol-ω-hydroxylase, and thus increase the amount and prolong the availability of these compounds in plasma and tissue.

8 Claims, 3 Drawing Sheets

TOCOPHEROL DERIVATIVES AND USES THEREOF

FIELD OF THE INVENTION

The invention relates to tocopherol derivatives and uses thereof. More specifically, it relates to tocopherol derivatives capable of inhibiting tocopherol-ω-hydroxylase activity.

BACKGROUND OF THE INVENTION

Vitamin E is comprised of eight different antioxidant compounds found in nature; four tocopherols and four tocotrienols. These two families differ from each other in the structure of the side chain, which is saturated in tocopherols and has three double bonds in the tocotrienols. The distinguishing feature within each family is the number and position of methyl groups attached to the chroman ring.

The tocopherols, namely α-tocopherol, β-tocopherol, γ-tocopherol and δ-tocopherol, are understood to be the major lipid soluble compounds in mammalian membranes. They act as chain-breaking inhibitors of free radical peroxidation of unsaturated fatty acids. Despite the fact that the diets of most North American individuals contain more γ-tocopherol than α-tocopherol, it is predominantly α-tocopherol that is retained in the body due to actions of a specific binding and transfer protein known as the tocopherol transfer protein (TTP). TTP is expressed mostly in liver tissue and has been shown to specifically bind α-tocopherol. The function of TTP is to aid in the secretion of the vitamin in lipoproteins such as very-low-density-lipoprotein that then carry the vitamin to remote tissues of the body. Interestingly, the other forms of vitamin E, besides α-tocopherol, are poorly retained by the body and are rapidly metabolized to water-soluble compounds for excretion in urine or transported to bile.

The metabolism of non-retained tocopherols (i.e., non-α-tocopherol and tocotrienols) is initiated in human cells by a cytochrome P450 monooxygenase, Cyp4F2, and its orthologs in other species. The enzyme activity is referred to as tocopherol-ω-hydroxylase. This enzyme metabolizes all forms of vitamin E by placing a hydroxyl group at the terminus of the side chain.

Recently it has been noted that γ-tocopherol and the tocotrienols have biological activities that are different from α-tocopherol. γ-tocopherol is known to act as an anti-inflammatory possibly by mechanisms different than α-tocopherol (Samandari E et al., (2006) Biochem Biophys Res Commun 342: 1329-33; Mazlan M et al., (2006) J Neurol Sci., 243(1-2): 5-12; Campbell S E, et al., (2006) BMC Cancer 6:13, Wu J H Y et al., (2005) Free Rad Res 39: S84-S84; Devaraj S et al., (2005) Nutr Rev 63: 290-293; Wagner K H et al. (2004) Annals Nutr Metab 48: 169-188; Jiang Q et al., (2004) Proc Natl Acad Sci U.S.A. 101: 17825-30; Grammas P et al., (2004) Biochem Biophys Res Commun 319: 1047-1052; Jiang Q et al., (2001) Am J Clin Nutr 74: 714-22) and to scavenge reactive nitrogen species such as peroxynitrite (Wolf G (1997) Nutr Rev 55: 376-378; Christen S et al., (1997) Proc Natl Acad Sci USA 94: 3217-22). The tocotrienols have been demonstrated to have significantly different biological activities from the tocopherols (Theriault A et al., (1999) Clin. Biochem. 32: 309-319), including inhibition of cholesterol biosynthesis (Parker R A et al., (1993) J Biol Chem 268: 11230-8; Pearce B C et al., (1994) J Med Chem 37: 526-41; Pearce B C et al., (1992) J Med Chem 35: 3595-606), anti-cancer effects (Nesaretnam K et al., (1998) Lipids 33: 461-469; Sylvester P W et al., (2005) Front Biosci 10: 699-709; Sylvester P W et al., (2005) J Plant Physiol 162: 803-810), and more recently for protection against glutamate-induced neurodegeneration in animal models of stroke (Khanna S et al., (2005) Stroke 36: E144-E152; Khanna S et al., (2003) J Biol Chem 278: 43508-15; Sen C K et al., (2004) Vitamin E And Health pp 127-142; Sen C K et al., (2000) J Biol Chem 275: 13049-13055).

To fully realize the promising biological activities of γ-tocopherol and the tocotrienols requires overcoming the poor bioavailability after ingestion. The primary reason for their poor bioavailability and short plasma half-lives is their rapid oxidative metabolism by tocopherol-ω-hydroxylase.

Since it has been discovered that non-α-tocopherols and the tocotrienols have desirable biological activities, there is a need to identify mechanisms that prolong their bioavailability. Based on the foregoing comments, one potential way to increase the bioavailability of non-α-tocopherols and tocotrienols is to develop compounds that decrease tocopherol-ω-hydroxylase activity.

SUMMARY OF THE INVENTION

Accordingly, an object of the present invention is to provide compounds that can inhibit tocopherol-ω-hydroxylase activity.

A further object of the present invention is to provide a method of synthesizing compounds that can inhibit tocopherol-ω-hydroxylase activity.

A yet further object of the present invention is to provide a method of therapeutically inhibiting the activity of tocopherol-ω-hydroxylase for a therapeutic purpose.

According to a first aspect of the present invention, there is provided α-tocopherol derivatives having the general formula:

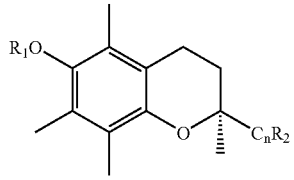

wherein n is an integer of 6 to 13, $R_1$ is hydrogen, a silyl ether or acetate, $R_2$ is an optionally substituted nitrogen-containing heterocycle or a polycyclic nitrogen-containing heterocycle.

Preferably, the $R_2$ group is selected from the group consisting of imidazoles, triazoles, tetrazoles, benzimidazole, benzotriazoles, pyrimidines, and pyrazines.

According to an embodiment of the present invention, the tocopherol derivative is selected from the group consisting of (R)-2-(9-(1H-imidazol-1-yl)nonyl)-2,5,7,8-tetramethylchroman-6-ol; (R)-1-(9-(6-(tert-butyldimethylsilyloxy)-2,5,7,8-tetramethylchroman-2-yl)nonyl)-1H-1,2,3-triazole; (R)-1-(9-(6-(tert-butyldimethylsilyloxy)-2,5,7,8-tetramethylchroman-2-yl)nonyl)-1H-1,2,4-triazole; (R)-2-(9-(1H-1,2,4-triazol-1-yl)nonyl)-2,5,7,8-tetramethylchroman-6-ol; (R)-2-(9-(1H-1,2,3-triazol-1-yl)nonyl)-2,5,7,8-tetramethylchroman-6-ol; (R)-2-(9-(6-(tert-butyldimethylsilyloxy)-2,5,7,8-tetramethylchroman-2-yl)nonyl)-2H-1,2,3-triazole; (R)-2-(9-(2H-1,2,3-triazol-2-yl)nonyl)-2,5,7,8-tetramethylchroman-6-ol; (R)-1-(9-(6-(tert-butyldimethylsilyloxy)-2,5,7,8-tetramethylchroman-2-yl)nonyl)-1H-benzo[d]imidazole; (R)-2-(9-(1H-benzo[d]imidazol-1-yl)nonyl)-2,5,7,8-tetramethylchroman-6-ol; (R)-2-(9-(6-(tert-butyldimethylsilyloxy)-2,5,7,8- tetramethylchroman-2-yl)nonyl)-2H-benzo[d][1,2,3] triazole; (R)-2-(9-(2H-benzo[d][1,2,3]triazol-2-yl)nonyl)-2, 5,7,8-tetramethylchroman-6-ol; (R)-1-(9-(6-(tert-butyldimethylsilyloxy)-2,5,7,8-tetramethylchroman-2-yl) nonyl)-1H-benzo[d][1,2,3]triazole; (R)-2-(9-(1H-benzo[d] [1,2,3]triazol-1-yl)nonyl)-2,5,7,8-tetramethylchroman-6-ol; 1-{9-[(R)-6-hydroxy-2,5,7,8-tetramethyl-chroman-2-yl]-nonyl}-5H-pyrimidine; and 1-{9-[(R)-6-hydroxy-2,5,7,8-tetramethyl-chroman-2-yl]-nonyl}-2H-pyrazine.

According to a second aspect of the present invention, there is provided a method for the synthesis of tocopherol derivatives of the general formula:

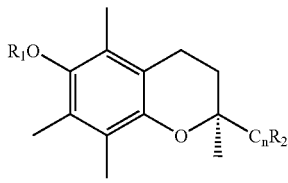

wherein n is 9 and $R_1$ is hydrogen or a silyl ether and $R_2$ is selected from the group consisting of optionally substituted imidazoles, triazoles, benzimidazoles and benzotriazoles; comprising the steps of: reacting (R)-9-(6-ter-butyl-dimethyl-silanyloxy)-2,5,7,8-tetramethylchroman-2-yl)nonyl methansulfonate with an optionally substituted imidazole, triazole, benzimidazole or benzotriazole.

According to a third aspect of the present invention, there is provided a method of therapeutically inhibiting the activity of tocopherol-ω-hydroxylase comprising administering a therapeutically effective amount of a tocopherol derivative, to a mammal in need thereof for a therapeutic purpose.

In particular, the compounds can be used in the treatment or prophylaxis of inflammation, hypercholesterolaemia, diabetes, circulatory shock, neurodegenerative disorders, cancers and ischaemia, including stroke and post-blockage re-perfusion oxidative stress in humans. Similarly, the compounds may be used for veterinarian or experimental purposes.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
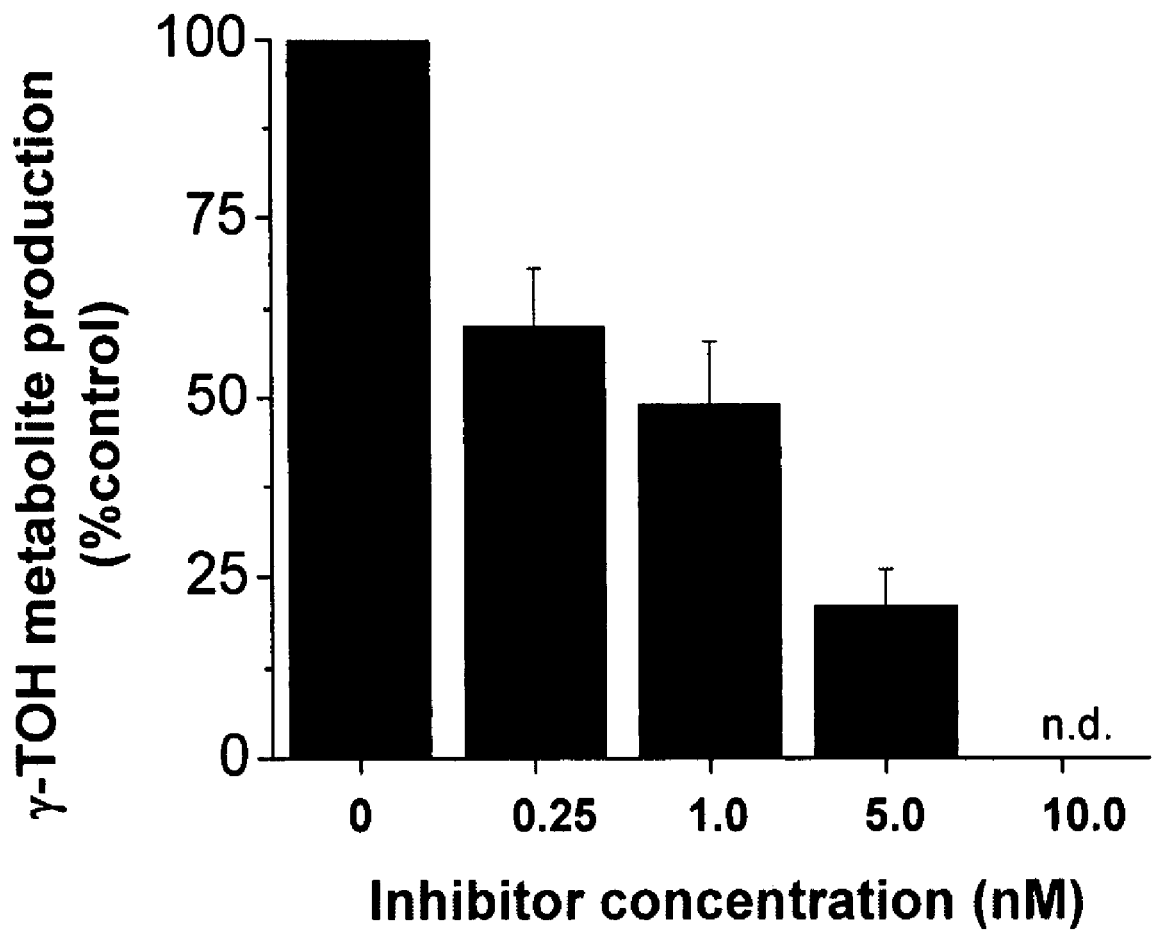
FIG. 1 shows the inhibition of metabolism of γ-tocopherol in HEPG2/C3A cultures by (R)-2-(9-(1H-imidazol-1-yl) nonyl)-2,5,7,8-tetramethylchroman-6-ol.

Tocopherol derivatives having the general formula:

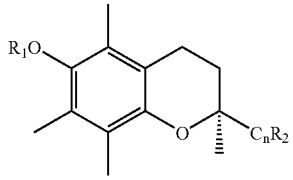

wherein n is an integer of 6 to 13, preferably 6 to 9 and more preferably 9; $R_1$ is hydrogen, silyl ether or acetate; $R_2$ is an optionally substituted nitrogen-containing heterocycle or a polycyclic nitrogen-containing heterocycle are shown to inhibit the tocopherol-ω-hydroxylase activity of cytochrome P450 monooxygenase. In particular, tocopherol derivatives where the phytyl side chain of α-tocopherol has been modified to incorporate a nitrogen heterocycle or polycyclic nitrogen-containing heterocycle are believed to act as ligands at the heme-iron atom of the cytochrome P450 monooxygenase and thus inhibit the tocopherol-ω-hydroxylase activity of the enzyme.

In an embodiment of the invention the phytyl side chain of the α-tocopherol derivatives has been modified to remove branching methyl groups and incorporate an imidazole, triazole, tetrazole, benzimidazole, benzotriazole, pyrimidine, or pyrazine. Each nitrogen-containing heterocycle may be optionally substituted, so long as the substituent does not increase the size of the heterocycle to a point where it can no longer be accommodated in the active site of the P450 monooxygenase enzyme. For example, alkylating an imidazole group will make the nitrogens more basic and better donors at the iron atom of P450 monoxygenase. Accordingly, preferred optionally substituents for nitrogen-containing heterocycle include: methyl, ethyl, propyl, iso-propyl, n-butyl, and sec-butyl. In addition, the benzimidazoles and benzotriazoles may be substituted on the aryl ring with hydroxyl, methoxy or alkyl.

The structure of the tocopherol derivatives is illustrated as a single enantiomer, however, it will be appreciated by those of ordinary skill in the art that the present invention is directed to both enantiomeric forms. Those of ordinary skill in the art will also appreciate that enrichment in one enantiomeric form can be achieved by conventional methods known to those of ordinary skill in the art, such as by chromatography, crystallization, diastereomeric separation or starting from optically enriched starting materials.

In a preferred embodiment of the invention, the side chain contains 9 carbons atoms. However, tocopherols with side chains containing 6 to 13 carbon atoms are able to bind tocopherol transfer protein and thus have biological activity (Ingold K U et al., (1992) Free Radical Biol. Med. 9:205-210; Nava P et al., (2006) Bioorg Med Chem 14:3721-3736).

The compounds of the present invention may also comprise a salt. Suitable pharmaceutically acceptable salts are known to those of ordinary skill in the art and comprise carboxylates, sulfates, phosphates and halides.

The tocopherol derivatives having the phytyl side chain of the α-tocopherol derivatives modified to incorporate an optionally substituted imidazole, triazole, tetrazole or benzimidazole can be synthesized by reacting (R)-9-(6-ter-butyl-dimethyl-silanyloxy)-2,5,7,8-tetramethylchroman-2-yl)

nonyl methansulfonate with an optionally substituted imidazole, triazole, benzimidazole or benzotriazole.

The compounds of the present invention inhibit the metabolism γ-tocopherol in vitro in HepG2/C3A cells and δ-tocopherol in vivo in mice fed a diet containing such compounds. Accordingly, such compounds are useful in the treatment of inflammation, hypercholesterolaemia, diabetes, circulatory shock, neurodegenerative disorders, cancers and ischaemia, including stroke and post-blockage re-perfusion oxidative stress. In addition, different does and pharmaceutical preparations may be used prophylactically for the prevention of any one of these conditions.

Having generally described this invention, a further understanding can be obtained by reference to certain specific examples which are provided herein for purposes of illustration only and are not intended to be limiting unless otherwise specified.

(R)-9-(6-tert-butyl-dimethyl-silanyloxy)-2,5,7,8-tetramethylchroman-2-yl)nonyl methanesulfonate 500 mg (1.08 mmol) of (R)-9-(6-tert-butyl-dimethyl-silanyloxy)-2,5,7,8-tetramethylchroman-2-yl)nonanol was dissolved in dry DCM (10 ml) under argon atmosphere, followed by the addition of triethylamine (224 ul), MsCl (mesylchloride) (125 ul) and a catalytic amount of DMAP (dimethyl amino pyridine) at 0° C. After 15 minutes the cooling bath was removed and the reaction stirred at room temperature for 1.5 hours. TLC monitoring showed complete conversion in 100% DCM as mobile phase. Extraction with water and DCM afforded crude product that was obtained following evaporation of the solvent under reduced pressure. Column chromatography on silica (100% DCM) gave pure (R)-9-(6-tert-butyl-dimethyl-silanyloxy)-2,5,7,8-tetramethylchroman-2-yl)nonyl methanesulfonate in high yields (following high vacuum). (90%, 526 mg, 0.97 mmol)

TLC: $R_f$=0.50 (100% DCM)

$^1$H-NMR (CDCl$_3$); δ 4.24 (t, 2H, C4-CH$_2$, J=6.408), 3.02 (s, 3H, OCH$_3$), 2.57 (t, 2H, O—CH$_2$, J=6.782), 2.12 (s, 3H, Ar—CH$_3$), 2.09 (s, 3H, Ar—CH$_3$), 2.07 (s, 3H, Ar—CH$_3$), 1.80 (m, 1H, C4-H)

$^{13}$C-NMR (CDCl$_3$); δ 145.90, 144.07, 125.85, 123.53, 122.66, 117.51, 74.46, 70.19, 39.58, 37.39, 31.55, 30.11, 29.49, 29.37, 29.14, 29.03, 26.12, 25.42, 23.83, 23.60, 20.91, 18.62, 14.34, 13.41, 11.96, −3.34

MS[EI+] m/z 540 (M+, 3%), 444 (13.4%), 97 (56.2%), 57 (100%)

HRMS (EI): calculated for C$_{29}$H$_{52}$O$_5$SSi: 540.330475 g/mol. Found 540.32732 g/mol (R)-2-(9-(1H-imidazol-1-yl)nonyl)-2,5,7,8-tetramethylchroman-6-ol A solution of (R)-9-(6-ter-butyl-dimethyl-silanyloxy)-2,5,7,8-tetramethylchroman-2-yl)nonyl methansulfonate (500 mg, 0.924 mmol) in dry ACN (5 ml) was added dropwise at room temperature under argon to a suspension of imidazole (126 mg, 1.849 mmol), KOtBu (207 mg, 1.849 mmol) and 18-crown-6-ether (25 mg, 0.0924 mmol) in dry ACN (10 ml). The mixture was refluxed (90° C.) under argon atmosphere for 15 hours. After cooling to room temperature, the resulting white precipitate was filtered off and the remaining organic phase acidified to pH 6 using 10% HCl. The reaction was then diluted with DCM (50 ml), washed several times with dH2O (3×30 ml), dried with Na2SO4, decanted, and concentrated under reduced pressure to give a brown oil. The crude product was purified by column chromatography (DCM to DCM/MeOH 100:1.5) to yield the desired product as a light yellow oil (260 mg, 71%).

$^1$H-NMR (CDCl$_3$); δ 7.48 (s, 1H), 7.07 (s, 1H), 6.91 (s, 1H), 3.91 (t, 2H, J=7.1 Hz), 2.63 (t, 2H, J=~6 Hz), 2.24 (s, 3H), 2.19 (s, 3H), 2.15 (s, 3H), 1.89-1.69 (m, 4H), 1.66-1.53 (m, 2H), 1.49-1.41 (m, 2H), 1.311 (br m, 10H), 1.27 (s, 3H), $^{13}$C-NMR (CDCl$_3$); δ 145.32, 136.90, 128.91, 122.75, 122.20, 120.21, 118.84, 117.13, 74.35, 53.53, 47.10, 39.53, 31.68, 31.04, 30.11, 29.50, 29.38, 29.09, 26.53, 23.91, 23.62, 20.86, 12.78, 11.89, 11.83.

MS[EI+] For C$_{25}$H$_{38}$N$_2$O$_2$; m/z 398 (M$^+$, 79%), 387 (13%), 235 (100%), 203 (10%), 179 (9%), 165 (26%). 137 (13%), 123 (10%), 96 (11%).

HRMS (EI): calculated for C$_{25}$H$_{38}$N$_2$O$_2$: 398.29333. Found 398.29336

(R)-1-(9-(6-(tert-butyldimethylsilyloxy)-2,5,7,8-tetramethylchroman-2-yl)nonyl)-1H-1,2,3-triazole A solution of (R)-9-(6-ter-butyl-dimethyl-silanyloxy)-2,5,7,8-tetramethylchroman-2-yl)nonyl methansulfonate (110 mg, 0.200 mmol) in dry ACN (2 ml) was added dropwise at room temperature under argon to a suspension of 1H-1,2,3-triazole (27 mg, 0.400 mmol), KOtBu (45 mg, 0.400 mmol) and 18-crown-6-ether (5 mg, 0.020 mmol) in dry ACN (4 ml). The mixture was refluxed (90° C.) under argon atmosphere for 15 hour. Upon cooling to room temperature, the resulting white precipitate was filtered off and the remaining organic phase acidified to pH 6 using 10% HCl. The reaction was then diluted with DCM (25 ml), washed several times with dH$_2$O (3×20 ml), dried with Na$_2$SO4, decanted, and concentrated under vacuum to give a yellow oil. The crude material was purified by column chromatography (DCM to Et$_2$O) affording the product as a clear colourless oil. (42 mg, 40%) $R_f$=0.42 (Et$_2$O).

$^1$H-NMR (CDCl$_3$); δ 7.71 (s, 1H), 7.54 (s, 1H), 4.39 (t, 2H, J=7.2 Hz), 2.56 (t, 2H, J=6.7 Hz), 2.11 (s, 3H), 2.08 (s, 3H), 2.07 (s, 3H), 1.92 (m, 2H), 1.79 (m, 2H, J=6.9 Hz), 1.65-1.49 (m, 2H), 1.45 (m, 2H), 1.32-1.28 (m, 10H), 1.23 (s, 3H), 1.06 (s, 9H), 0.132 (s, 6H).

$^{13}$C-NMR (CDCl$_3$); δ 145.90, 144.06, 133.73, 125.82, 123.52, 123.10, 122.64, 117.50, 74.44, 50.18, 39.55, 31.55, 30.33, 30.07, 29.44, 29.31, 28.97, 26.45, 26.11, 23.82, 23.57, 20.90, 18.60. 14.33, 13.41, 11.96, −3.33

MS[EI+] For C$_{30}$H$_{51}$N$_3$O$_2$Si; m/z 513 (M+, 17%), 205 (10%), 129 (10%), 82 (100%)

HRMS (EI): calculated for C$_{30}$H$_{51}$N$_3$O$_2$Si: 513.37506. Found 513.37517

(R)-2-(9-(1H-1,2,3-triazol-1-yl)nonyl)-2,5,7,8-tetramethylchroman-6-ol

A solution of tetrabutylammonium fluoride (TBAF) (1M in THF, 250 μL) was added dropwise via syringe to a stirred solution of (R)-1-(9-(6-(tert-butyldimethylsilyloxy)-2,5,7,8-tetramethylchroman-2-yl)nonyl)-1H-1,2,3-triazole (65 mg, 0.126 mmol) in dry THF (5 ml). The mixture was stirred at room temperature for 30 minutes until starting material was not detected by TLC. The reaction was then quenched with 500 μL of 1N HCl and diluted with 25 ml of ether, to which an additional 10 ml of dH$_2$O was added. The water phase was extracted again with ether (2×25 ml), dried over anhydrous Na$_2$SO4, filtered, and concentrated under reduced pressure. The crude product was chromatographed on silica gel (Et$_2$O) to give the pure product (TLC $R_f$=0.49, EtOAc) as an off-white/yellow solid. (35 mg, 70%)

¹H-NMR (CDCl₃); δ 7.71 (s, 1H), 7.54 (s, 1H), 4.55 (s, 1H), 4.39 (t, 2H, J=7.2 Hz), 2.62 (t, 2H, J=6.7 Hz), 2.18 (s, 3H), 2.13 (s, 3H), 2.12 (s, 3H), 1.91 (m, 2H), 1.79 (m, 2H, J=6.9 Hz), 1.65-1.51 (m, 2H), 1.48-1.41 (m, 2H), 1.32-1.28 (m, 10H), 1.24 (s, 3H).

¹³C-NMR (CDCl₃); δ 145.55, 144.65, 133.72, 123.12, 122.52, 121.24, 118.71, 117.32, 74.45, 50.20, 39.45, 31.55, 30.33, 30.04, 29.43, 29.29, 28.97, 26.44, 23.82, 23.55, 20.76, 12.29, 11.80, 11.35.

MS[EI+] For $C_{24}H_{37}N_3O_2$ 399.6 (M+, 68%), 236 (20%) 205 (12%), 203 (21%), 165 (100%), 121 (11%),

HRMS (EI): calculated for $C_{24}H_{37}N_3O_2$: 399.28858. Found 399.28812

(R)-1-(9-(6-(tert-butyldimethylsilyloxy)-2,5,7,8-tetramethylchroman-2-yl)nonyl)-1H-1,2,4-triazole (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with 1,2,4-triazole. The product was a clear colourless oil. $R_f$ 0.4 (EtOAc). Purified by silica gel column chromatography using 100% Et₂O.

¹H-NMR (CDCl₃); δ 8.04 (s, 1H), 7.94 (s, 1H), 4.15 (t, 2H, J=7 Hz), 2.56 (t, 2H, J=6.5 Hz), 2.11 (s, 3H), 2.08 (s, 3H), 2.07 (s, 3H), 1.83 (m, 2H), 1.76 (m, 2H, J=6.6 Hz), 1.61-1.49 (m, 2H), 1.42 (m, 2H), 1.28 (m, 10H), 1.23 (m, 3H), 1.06 (s, 9H), 0.13 (s, 6H)

¹³C-NMR (CDCl₃); δ 151.85, 145.90, 144.06, 125.81, 123.49, 122.63, 117.47, 74.42, 49.69, 39.54, 31.55, 30.07, 29.77, 29.44, 29.32, 28.99, 26.43, 26.12, 23.83, 23.56, 20.90, 18.60, 14.34, 13.41, 11.96, −3.33.

MS[EI+] For $C_{30}H_{51}N_3O_2Si$; m/z 513 (M+, 37%), 221 (11%), 205 (24%), 149 (12%), 138 (10%), 129 (14%).

HRMS (EI): calculated for $C_{30}H_{51}N_3O_2Si$: 513.37506. Found 513.37517

(R)-2-(9-(1H-1,2,4-triazol-1-yl)nonyl)-2,5,7,8-tetramethylchroman-6-ol (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with 1,2,4-triazole. The product was an off white solid. $R_f$ 0.31 (EtOAc). Purified by silica gel column chromatography using 100% Et₂O.

¹H-NMR (CDCl₃); δ 8.03 (s, 1H), 7.93 (s, 1H), 5.13 (s, 1H), 4.14 (t, 2H, J=7 Hz), 2.59 (t, 2H, J=6.5 Hz), 2.16 (s, 3H), 2.11 (s, 3H), 2.10 (s, 3H), 1.86 (m, 2H), 1.76 (m, 2H, J=6.6 Hz), 1.59-1.49 (m, 2H), 1.43 (m, 2H), 1.28 (m, 10H), 1.23 (m, 3H).

¹³C-NMR (CDCl₃); δ 151.73, 144.49, 144.74, 142.76, 122.47, 117.28, 74.43, 49.75, 39.44, 31.58, 30.04, 29.76, 29.43, 29.30, 28.99, 26.42, 23.84, 23.55, 20.78, 12.42, 11.81.

MS[EI+] For $C_{24}H_{37}N_3O_2$; m/z 399 (M+, 68%), 236 (16%), 205 (12%), 203 (13%), 165 (100%), 121 (11%).

HRMS (EI): calculated for $C_{24}H_{37}N_3O_2$: 399.28858. Found 399.28924

(R)-2-(9-(6-(tert-butyldimethylsilyloxy)-2,5,7,8-tetramethylchroman-2-yl)nonyl)-2H-1,2,3-triazole (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with 1,2,3-triazole. The product was a clear colourless oil. $R_f$=0.41 (DCM). Purified by silica gel column chromatography using 100% DCM to 100% Et₂O.

¹H-NMR (CDCl₃); δ 7.60 (s, 2H), 4.46 (t, 2H, J=7.1 Hz), 2.57 (t, 2H, J=6.8 Hz), 2.12 (s, 3H), 2.10 (s, 3H), 2.08 (s, 3H), 1.98 (m, 2H, J=6.7 Hz), 1.74 (m, 2H, J=7.1 Hz), 1.62-1.52 (m, 2H), 1.50-1.42 (m, 2H), 1.37-1.29 (m, 10H), 1.24 (s, 3H), 1.07 (s, 9H), 0.143 (s, 6H).

¹³C-NMR (CDCl₃); δ 145.91, 144.07, 133.79, 125.84, 123.50, 122.67, 117.49, 74.45, 54.88, 39.59, 31.55, 30.11, 29.75, 29.47, 29.35, 29.02, 26.47, 26.13, 23.83, 23.61, 20.91, 18.62, 14.34, 13.41, 11.96, −3.2

MS[EI+] For $C_{30}H_{51}N_3O_2Si$; m/z 513 (M+, 83%), 332 (12%), 317 (10%), 279 (20%), 221 (20%), 220, (21%), 168 (44%), 128 (12%).

HRMS (EI): calculated for $C_{30}H_{51}N_3O_2Si$: 513.37506. Found 513.37446.

(R)-2-(9-(2H-1,2,3-triazol-2-yl)nonyl)-2,5,7,8-tetramethylchroman-6-ol (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with 1,2,3-triazole. The product was an off-white solid, $R_f$=0.60 (EtOAc) Purified by silica gel column chromatography using 100% Et₂O.

¹H-NMR (CDCl₃); δ 7.61 (s, 2H), 4.45 (t, 2H, J=7.3 Hz), 4.42 (br s, 1H), 2.62 (t, 2H, J=6.8 Hz), 2.18 (s, 3H), 2.13 (s, 6H), 2.04-1.94 (m, 2H), 1.88-1.73 (m, 2H), 1.66-1.49 (m, 2H), 1.28 (brs, 10H), 1.24 (s, 3H).

¹³C-NMR (CDCl₃); δ 144.58, 133.80, 122.58, 121.18, 118.65, 117.34, 74.47, 54.89, 39.42, 31.56, 30.05, 29.75, 29.43, 29.30, 29.00, 26.45, 23.83, 23.56, 20.77, 12.26, 11.79, 11.32.

MS[EI+] For $C_{24}H_{37}N_3O_2$; m/z 399 (M+, 36%), 231 (10%), 165 (78%), 122 (20%), 106 (21%), 79 (100%).

HRMS (EI): calculated for $C_{24}H_{37}N_3O_2$: 399.28858. Found 399.28895

(R)-1-(9-(6-(tert-butyldimethylsilyloxy)-2,5,7,8-tetramethylchroman-2-yl)nonyl)-1H-benzo[d]imidazole (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with a benzo[d]imidazole. The product was a clear colourless oil. $R_f$ 0.45 (EtOAc). Purified by silica gel column chromatography using DCM:Et₂O (3:2).

¹H-NMR (CDCl₃); δ 7.91 (s, 1H), 7.85 (m, 1H), 7.44-7.41 (m, 1H), 7.35-7.28 (m, 2H), 4.19 (t, 2H, J=7.1 Hz), 2.58 (t, 2H, J=6.5 Hz), 2.14 (s, 3H), 2.11 (s, 3H), 2-10 (s, 3H), 1.94-1.84 (m, 2H), 1.82-1.75 (m, 2H), 1.67-1.51 (m, 2H), 1.53-1.43 (m, 2H), 1.34-1.30 (m, 10H), 1.26 (s, 3H), 1.09 (s, 9H), 0.159 (s, 6H).

¹³C-NMR (CDCl₃); δ 145.93, 144.09, 143.90, 142.94, 133.85, 125.84, 123.53, 122.78, 122.67, 122.00, 120.40, 117.52, 109.68, 74.45, 45.10, 39.57, 31.58, 30.10, 29.49, 29.39, 29.12, 26.83, 26.15, 23.86, 23.59, 20.93, 18.63, 14.37, 13.45, 12.00, −3.30

MS[EI+] For $C_{35}H_{54}N_2O_2Si$; m/z 562 (M+, 11%), 258 (13%), 230 (17%), 229 (14%), 220 (28%), 205 (100%), 201 (11%), 189 (22%), 187 (19%), 136 (25%), 124 (16%), 122 (20%).

HRMS (EI): calculated for $C_{35}H_{54}N_2O_2Si$: 562.39546. Found 562.39774

(R)-2-(9-(1H-benzo[d]imidazol-1-yl)nonyl)-2,5,7,8-tetramethylchroman-6-ol (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with benzo[d]imidazole. The product was a light yellow oil, $R_f$=0.31 (EtOAc). Purified by silica gel column chromatography using DCM:Et$_2$O (3:2).

$^1$H-NMR (CDCl$_3$); δ 7.90 (s, 1H), 7.84-7.81 (m, 1H), 7.44-7.40 (m, 1H), 7.33-7.29 (m, 2H), 5.15 (br s, 1H), 4.17 (t, 2H, J=7.1 Hz), 2.62 (t, 2H, J=6.5 Hz), 2.20 (s, 3H), 2.15, (s, 3H), 2.13 (s, 3H), 1.91-1.85 (m, 2H), 1.81-1.71 (m 2H), 1.66-1.54 (m, 2H), 1.52-1.39 (m, 2H), 1.33-1.28 (m, 10H), 1.24 (s, 3H).

$^{13}$C-NMR (CDCl$_3$); δ 145.48, 144.77, 143.77, 142.89, 133.80, 122.80, 122.48, 122.04, 121.60, 120.36, 119.06, 117.29, 109.68, 74.43, 45.12, 39.42, 31.58, 30.05, 29.81, 29.44, 29.35, 29.09, 26.80, 23.86, 23.56, 20.78, 12.41, 11.81, 11.47

MS[EI+] For $C_{29}H_{40}N_2O_2$; m/z 448 (M$^+$, 1%), 437 (1%), 286 (11%), 243 (17%), 229 (25%), 205 (23%), 145 (12%), 131 (35%) 118 (28%), 86 (64%), 84 (100%)

HRMS (EI): calculated for $C_{29}H_{40}N_2O_2$: 448.30898. Found 448.30867

(R)-2-(9-(6-(tert-butyldimethylsilyloxy)-2,5,7,8-tetramethylchroman-2-yl)nonyl)-2H-benzo[d][1,2,3]triazole (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with benzo[d][1,2,3]triazole. The product was a clear colourless oil. $R_f$0.56 (DCM). Purified by silica gel column chromatography using 100% DCM to 100% Et$_2$O.

$^1$H-NMR (CDCl$_3$); δ 7.90 (ddd, 2H, J$_{1(apparent)}$=9.6 Hz, J$_{2(apparent)}$=3.1 Hz), 7.40 (ddd, 2H, J$_{1(apparent)}$=9.6 Hz, J$_{2(apparent)}$=3.1 Hz), 2.57 (t, 2H, J=6.7 Hz), 4.75 (t, 2H, J=7.1 Hz), 2.57 (t, 2H, J=6.2 Hz), 2.15 (obscured m, 2H, J=7.2 Hz), 2.13 (s, 3H), 2.13 (s, 3H), 2.10 (s, 3H), 1.92-1.72 (m, 2H, J=7.2 Hz), 1.66-1.50 (m, 2H), 1.47-1.38 (br m, 6H), 1.30 (br s, 6H), 1.24 (s, 3H).

$^{13}$C-NMR (CDCl$_3$); δ 145.92, 144.30, 126.13, 125.84, 123.50, 122.68, 117.97, 117.49, 74.45, 56.65, 39.59, 31.56, 30.09, 29.48, 29.32, 29.03, 26.57, 26.14, 23.83, 23.60, 20.93, 18.62, 14.35, 13.43, 11.97, −3.31.

MS[EI+] For $C_{34}H_{53}N_3O_2Si$; m/z 563 (M$^+$, 14%), 428 (13%), 307 (1−%), 243 (11−%), 229 (12%), 205 (30%), 167 (14%), 149 (69%), 132 (10%), 131 (17%), 120 (22%)

HRMS (EI): calculated for $C_{34}H_{53}N_3O_2Si$: 563.39071. Found 563.38909

(R)-2-(9-(2H-benzo[d][1,2,3]triazol-2-yl)nonyl)-2,5,7,8-tetramethylchroman-6-ol (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with benzo[d][1,2,3]triazole. The product was a light yellow oil, $R_f$=0.26 (DCM). Purified by silica gel column chromatography using 100% DCM to 100% Et$_2$O.

$^1$H-NMR (CDCl$_3$); δ 7.90 (ddd, 2H, J$_{1(apparent)}$=9.6 Hz, J$_{2(apparent)}$=3.1 Hz), 7.40 (ddd, 2H, J$_{1(apparent)}$=9.6 Hz, J$_{2(apparent)}$=3.1 Hz), 4.74 (t, 3H, J=7.1 Hz), 2.62 (t, 2H, J=6.7 Hz), ~2.14 (obscured m, 2H), 2.18 (s, 3H), 2.13 (s, 3H), 2.12 (s, 3H), 1.87-1.71 (m, 2H, J=6.8 Hz), 1.67 (s, 1H), 1.65-1.53 (m, 2H), 1.50-1.35 (br m, 6H), 1.28 (br m, 6H), 1.24 (s, 3H)

$^{13}$C-NMR (CDCl$_3$); δ 145.55, 144.56, 144.27, 126.16, 122.59, 121.14, 118.61, 117.94, 117.35, 74.47, 56.65, 39.41, 31.56, 30.07, 30.02, 29.43, 29.26, 29.01, 26.53, 23.83, 23.55, 20.76, 12.26, 11.79, 11.32.

MS[EI+] For $C_{28}H_{39}N_3O_2$; m/z 449 (M$^+$, 46%), 399 (13%), 165 (100%), 120 (16%)

HRMS (EI): calculated for $C_{28}H_{39}N_3O_2$: 449.30423 Found 449.30397

(R)-1-(9-(6-(tert-butyldimethylsilyloxy)-2,5,7,8-tetramethylchroman-2-yl)nonyl)-1H-benzo[d][1,2,3]triazole (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with benzo[d][1,2,3]triazole. The product was a clear colourless oil. $R_f$0.19 (DCM). Purified by silica gel column chromatography using 100% DCM to 100% Et$_2$O.

$^1$H-NMR (CDCl$_3$); δ 8.08 (d, 1H, J=7.3 Hz), 7.52 (m, 2H), 7.38 (m, 1H), 4.65 (t, 2H, J=7.1 Hz), 2.57 (t, 2H, J=6.7 Hz), 2.12 (s, 3H), 2.10 (s, 3H), 2.08 (s, 3H), 2.03 (m, 2H), 1.92-1.72 (m, 2H), 1.65-1.52 (m, 6H), 1.49-1.36 (br m, 6H), 1.28 (s, 3H), 1.07 (s, 9H), 0.144 (s, 6H).

$^{13}$C-NMR (CDCl$_3$); δ 145.91, 144.08, 132.97, 127.11, 125.82, 123.74, 123.51, 122.65, 120.03, 117.50, 109.34, 74.45, 48.23, 39.57, 31.56, 30.08, 29.70, 29.47, 29.33, 29.04, 26.72, 26.14, 23.84, 23.58, 20.92, 18.62, 14.36, 13.43, 11.97, −3.31.

MS[EI+] For $C_{34}H_{53}N_3O_2Si$; m/z 563 (M$^+$, 14%), 506 (3%), 259 (6%), 250 (5%), 221 (5%), 205 (4%), 174 (5%), 149 (16%),

HRMS (EI): calculated for $C_{34}H_{53}N_3O_2Si$: 563.39071. Found 563.39020

(R)-2-(9-(1H-benzo[d][1,2,3]triazol-1-yl)nonyl)-2,5,7,8-tetramethylchroman-6-ol (R)-1-(9-(6-(tert-butyldimethylsilyloxy)-2,5,7,8-tetramethylchroman-2-yl)nonyl)-1H-1,2,4-triazole was synthesized as described above by reacting (R)-9-(6-ter-butyl-dimethyl-silanyloxy)-2,5,7,8-tetramethylchroman-2-yl)nonyl methansulfonate with benzo[d][1,2,3]triazole. The product was a light yellow oil, TLC $R_f$=0.55 (Et$_2$O). Purified by silica gel column chromatography using 100% DCM to 100% Et$_2$O.

$^1$H-NMR (CDCl$_3$); δ 8.08 (d, 1H, J=8.3 Hz), 7.52 (m, 2H), 7.38 (dt, 1H, J$_1$=7.3 Hz, J$_2$=0.9 Hz), 5.31 (s, 1H), 4.65 (t, 2H, J=7.1 Hz), 2.61 (t, 2H, J=6.8 Hz), 2.18 (s, 3H), 2.14 (s, 3H), 2.12 (s, 3H), 2.06-1.97 (m, 2H), 1.86-1.73 (m, 2H, J=6.8 Hz), 1.65-1.51 (m, 2H), 1.47-1.35 (bm, 6H), 1.27 (bs, 6H), 1.24 (s, 3H).

$^{13}$C-NMR (CDCl$_3$); δ 145.51, 144.64, 132.96, 127.13, 123.77, 122.54, 121.22, 120.03, 118.69, 117.33, 108.34, 74.45, 48.25, 39.46, 31.55, 30.04, 29.69, 29.44, 29.30, 29.03, 26.71, 23.81, 23.56, 20.77, 15.27, 12.29, 11.80, 11.35

MS[EI+] For $C_{28}H_{39}N_3O_2$ m/z 449 (M+, 41%), 438 (32%), 286 (13%), 205 (12%), 203 (17%), 165 (60%), 146 (13%), 137 (12%), 132 (21%), 120 (28%).

HRMS (EI): calculated for $C_{28}H_{39}N_3O_2$: 449.30423. Found 449.30393

Example 1

Effect of (R)-2-(9-(1H-1,2,4-triazol-1-yl)nonyl)-2,5,7,8-tetramethylchroman-6-ol on metabolism of γ-tocopherol in HepG2/C3A hepatoblastoma cultures (R)-2-(9-(1H-1,2,4-triazol-1-yl)nonyl)-2,5,7,8-tetramethylchroman-6-ol and γ-tocopherol stock solutions were prepared in ethanol. Confluent cultures of the human heptoblastoma cell line, HepG2/C3A, were pre-incubated with varying concentrations of (R)-2-(9-(1H-1,2,4-triazol-1-yl)nonyl)-2,5,7,8-tetramethylchroman-6-ol or ethanol for 4 hours, followed by addition of 25 µM γ-tocopherol. After 48 hours, culture media was collected and analyzed for ω-oxidation products of γ-tocopherol (the 3'- and 5'-carboxychromanols) by GC-MS, using $d_9$-3'-carboxyethylchromanol as internal standard (Sontag T J et al. (2002) J Biol Chem 277: 25290-25296).

Tocopherol hydroxylase activity was completely abolished at (R)-2-(9-(1H-1,2,4-triazol-1-yl)nonyl)-2,5,7,8-tetramethylchroman-6-ol concentrations above 10 nM. As shown in FIG. 1, the concentration required to inhibit activity by 50% ($EC_{50}$) was approximately 1 nM. There was no effect of (R)-2-(9-(1H-1,2,4-triazol-1-yl)nonyl)-2,5,7,8-tetramethylchroman-6-ol on cell protein and all monolayers appeared normal in morphology.

Example 2

Figure 2:
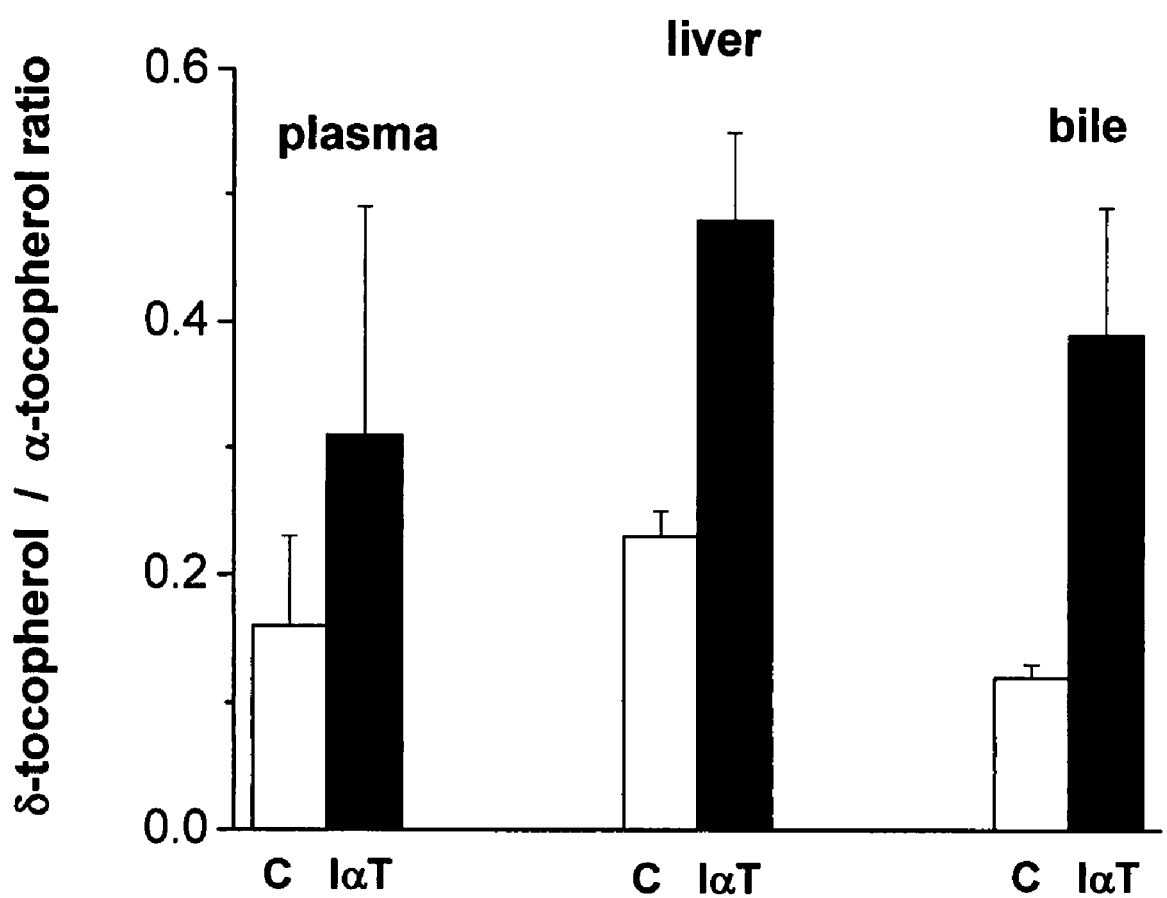
FIG. 2 shows the effect of (R)-2-(9-(1H-imidazol-1-yl) nonyl)-2,5,7,8-tetramethylchroman-6-ol on tissue enrichment in δ-tocopherol in mice. C, control; and IαT, (R)-2-(9-(1H-imidazol-1-yl)nonyl)-2,5,7,8-tetramethylchroman-6-ol. Data are shown as means of triplicate samples plus/minus standard deviation.

Effect of (R)-2-(9-(1H-1,2,4-triazol-1-yl)nonyl)-2,5,7,8-tetramethylchroman-6-ol on tissue enrichment in δ-tocopherol in mice in vivo Two groups of mice (n=3) were fed a chow diet enriched with δ-tocopherol (6000 mg per kg diet), with or without 500 mg per kg (R)-2-(9-(1H-1,2,4-triazol-1-yl)nonyl)-2,5,7,8-tetramethylchroman-6-ol. After 10 days on diet, mice were fasted for 5 hrs, euthanized, and tocopherol concentrations determined in plasma, liver and bile, using GC-MS procedures and $d_9$-3'-carboxyethylchromanol as internal standard (Sontag T J et al.).

α-tocopherol is a poor substrate for tocopherol hydroxylase, thus as expected there was no evidence that α-tocopherol status was affected by feeding α-tocopherol or (R)-2-(9-(1H-1,2,4-triazol-1-yl)nonyl)-2,5,7,8-tetramethylchroman-6-ol. Therefore data shown in FIG. 2 are presented as the δ-tocopherol/α-tocopherol ratio, where an increase in the ratio reflects enrichment in δ-tocopherol relative to α-tocopherol.

(R)-2-(9-(1H-1,2,4-triazol-1-yl)nonyl)-2,5,7,8-tetramethylchroman-6-ol feeding resulted in a doubling in the δ-tocopherol/α-tocopherol ratio in mouse liver (P<0.05). In addition, the corresponding ratio in bile was tripled in (R)-2-(9-(1H-imidazol-1-yl)nonyl)-2,5,7,8-tetramethylchroman-6-ol-fed mice (P<0.05), indicating that at least some of the unmetabolized γ-tocopherol was being secreted into bile.

Example 3

Effect of (R)-2-(9-(1H-1,2,4-triazol-1-yl)nonyl)-2,5,7,8-tetramethylchroman-6-ol and (R)-2-(1H-1,2,3-triazol-1-yl)nonyl)-2,5,7,8-tetramethylchroman-6-ol on metabolism of γ-tocopherol in HepG2/C3A cultures The effect of the triazole compounds were tested in human hepatoblastoma cell culture as described in Example 1, i.e. using 25 µM γ-tocopherol as substrate and 4 hour pre-incubation with the synthetic inhibitors.

Figure 3:
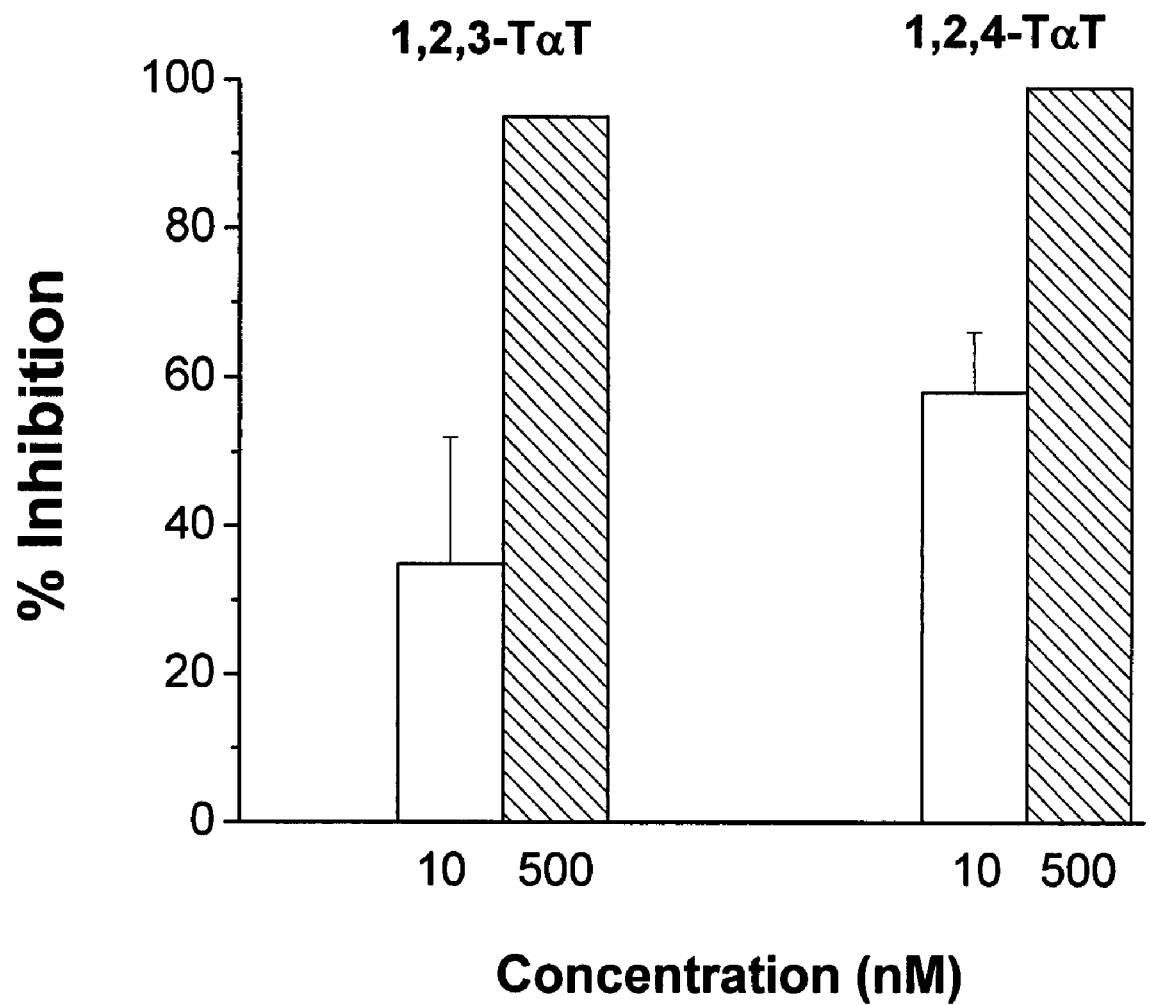
FIG. 3 shows the effect of (R)-1-(9-(6-(tert-butyldimethylsilyloxy)-2,5,7,8-tetramethylchroman-2-yl)nonyl)-1H-1, 2,4-triazole and (R)-1-(9-(6-(tert-butyldimethylsilyloxy)-2, 5,7,8 tetramethylchroman-2-yl)nonyl)-1H-1,2,3-triazole on metabolism of γ-tocopherol in HepG2/C3A cultures.

As shown in FIG. 3, both triazole compounds were effective at inhibiting tocopherol hydroxylase activity in HepG2/C3A cultures. Their potency was slightly less than that of (R)-2-(9-(1H-imidazol-1-yl)nonyl)-2,5,7,8-tetramethylchroman-6-ol, with $EC_{50}$ values of approximately 10 nM, compared to 1-2 nM for (R)-2-(9-(1H-imidazol-1-yl)nonyl)-2,5,7,8-tetramethylchroman-6-ol.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A compound having the formula:

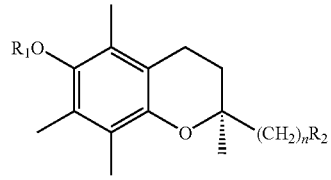

where n is an integer of 6 to 13;

$R_1$ is hydrogen, or a ter-butyl-dimethyl-silanyl or acetyl group;

$R_2$ is an imidazolyl group optionally substituted with a methyl, ethyl, propyl, isopropyl, n-butyl or sec-butyl group, or a benzimidazolyl group optionally substituted with a methyl, ethyl, propyl, isopropyl, n-butyl or sec-butyl group, said benzimidazolyl group being further optionally substituted on the aryl ring thereof with a hydroxy, methoxy, methyl, ethyl, propyl, isopropyl, n-butyl or sec-butyl group;

and pharmaceutically acceptable salts thereof.

2. The compound according to claim 1, wherein $R_2$ is a 1H-imidazol-1-yl or 1H-benzo[d]imidazolyl group.

3. The compound according to claim 1, wherein n is an integer of 6 to 9.

4. The tocopherol derivative compound according to claim 3, wherein n is the integer 9.

5. The compound according to claim 1, selected from the group consisting of (R)-2-(9-(1H-imidazol-1-yl)nonyl)-2,5,7,8-tetramethylchroman-6-ol; (R)-1-(9-(6-(tert-butyldimethylsilyloxy)-2,5,7,8-tetramethylchroman-2-yl)nonyl)-1-H- benzo[d]imidazole; and (R)-2-(9-(1H-benzo[d]imidazol-1-yl)nonyl)-2,5,7,8-tetramethylchroman-6-ol.

6. A method for the synthesis of a compound of the formula

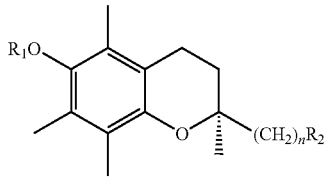

where
n is 9;
$R_1$ is hydrogen or a ter-butyl-dimethyl-silanyl group; and
$R_2$ is an imidazolyl group optionally substituted with a methyl, ethyl, propyl, isopropyl, n-butyl or sec-butyl group, or a benzimidazolyl group optionally substituted with a methyl, ethyl, propyl, isopropyl, n-butyl or sec-butyl group, said benzimidazolyl group being further optionally substituted on the aryl ring thereof with a hydroxy, methoxy, methyl, ethyl, propyl, isopropyl, n-butyl or sec-butyl group;

wherein the method comprises the steps of
reacting (R)-9-(6-ter-butyl-dimethyl-silanyloxy)-2,5,7,8-tetramethylchroman-2-yl)nonyl methansulfonate with imidazole, an imidazole optionally substituted with a methyl, ethyl, propyl, isopropyl, n-butyl or sec-butyl group, a benzimidazole or a benzimidazole optionally substituted with a methyl, ethyl, propyl, isopropyl, n-butyl or sec-butyl group, said substituted benzimidazole being further optionally substituted on the aryl ring thereof with a hydroxy, methoxy, methyl, ethyl, propyl, isopropyl, n-butyl or sec-butyl group;

optionally removing said ter-butyl-dimethyl-silanyl group; and recovering said compound.

7. The method of claim 6, wherein said step of optionally removing said ter-butyl-dimethyl-silanyl group is carried out using tetrabutylammonium fluoride (TBAF) in tetrahydrofuran (THF).

8. The method according to claim 6, wherein said compound is (R)-2-(9-(1H-imidazol-1-yl)nonyl)-2,5,7,8-tetramethylchroman-6-ol.

* * * * *